(12) United States Patent
Paul et al.

(10) Patent No.: US 8,285,029 B2
(45) Date of Patent: Oct. 9, 2012

(54) DEVICE AND METHOD FOR OPTICALLY SORTING BULK MATERIAL

(75) Inventors: Detlef Paul, Stutensee (DE); Matthias Burkhard, Karlsruhe (DE); Michal Palmer, Karlsruhe (DE); Matthias Hartrumpf, Karlsruhe (DE)

(73) Assignee: Fraunhofer-Gesellschaft zur Förderung der Angewandten Forschung e.V., Munich (DE)

( * ) Notice: Subject to any disclaimer, the term of this patent is extended or adjusted under 35 U.S.C. 154(b) by 628 days.

(21) Appl. No.: 12/447,040

(22) PCT Filed: Oct. 10, 2007

(86) PCT No.: PCT/EP2007/008795
§ 371 (c)(1),
(2), (4) Date: Nov. 20, 2009

(87) PCT Pub. No.: WO2008/049515
PCT Pub. Date: May 2, 2008

(65) Prior Publication Data
US 2010/0080456 A1     Apr. 1, 2010

(30) Foreign Application Priority Data

Oct. 25, 2006   (DE) .................. 20 2006 016 604 U

(51) Int. Cl.
*G06K 9/00*     (2006.01)

(52) U.S. Cl. ........................................................ 382/143
(58) Field of Classification Search ................... 382/143
See application file for complete search history.

(56) References Cited

U.S. PATENT DOCUMENTS

| | | | |
|---|---|---|---|
| 5,265,732 A | 11/1993 | Long | |
| 2003/0034282 A1 | 2/2003 | Safai | |
| 2006/0016735 A1* | 1/2006 | Ito et al. ........................ | 209/576 |

FOREIGN PATENT DOCUMENTS

| | | |
|---|---|---|
| DE | 203 20 957 U1 | 9/2003 |
| EP | 0 146 299 B1 | 6/1985 |
| EP | 0 223 446 B1 | 3/1991 |
| EP | 0 897 762 B1 | 8/1998 |
| GB | 2 091 416 A | 7/1982 |
| WO | WO 98/00243 | 1/1998 |

* cited by examiner

*Primary Examiner* — Roy M Punnoose
(74) *Attorney, Agent, or Firm* — Antonelli, Terry, Stout & Kraus, LLP.

(57) ABSTRACT

A device and a method are described for the optical selection of components of at least one fraction from a bulk material stream conveyed along a conveyance direction, having a camera unit, whose camera viewing direction is oriented toward the bulk material stream, a background, situated in the camera viewing direction behind the bulk material stream, whose color is adaptable to the color of a selected fraction of components of the bulk material stream, an analysis and control unit, connected to the camera unit, in which control commands for a separation unit, which is capable of separating the components to be selected out of the bulk material stream upon activation, may be generated according to a decision criterion.

Figure 1:
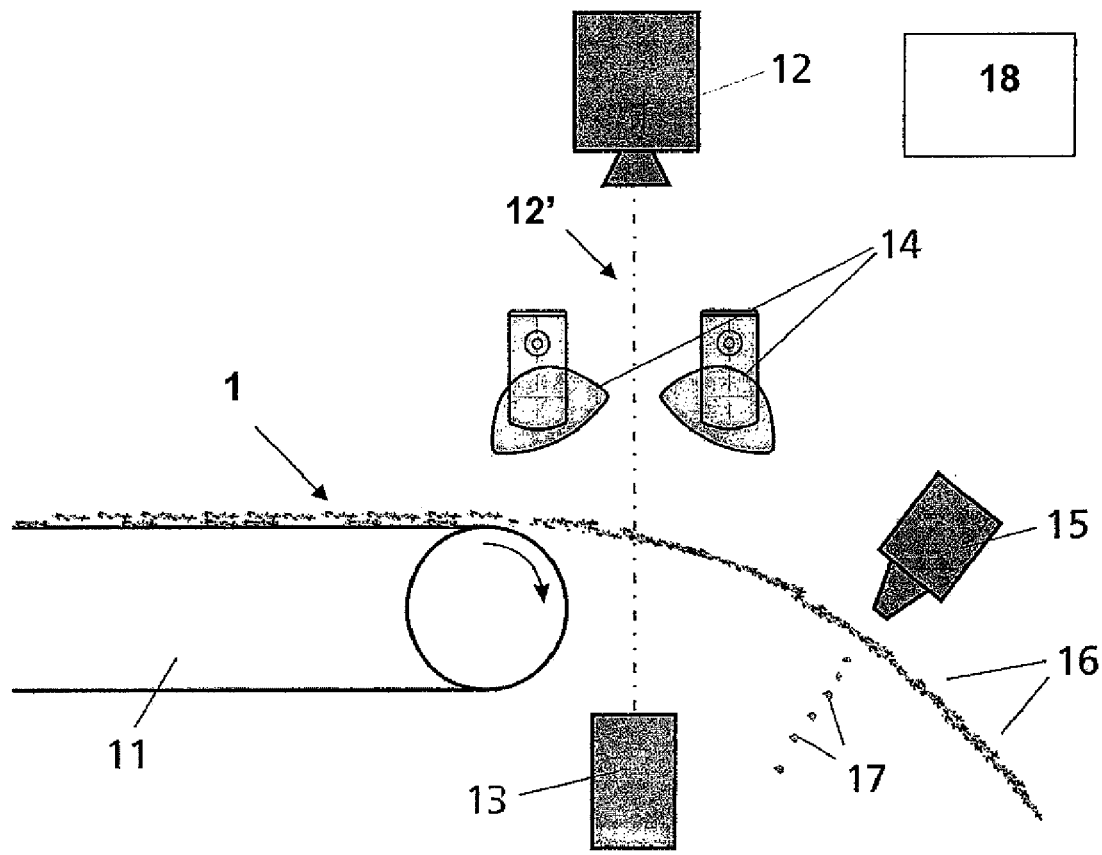

24 Claims, 4 Drawing Sheets

DEVICE AND METHOD FOR OPTICALLY SORTING BULK MATERIAL

BACKGROUND OF THE INVENTION

1. Field of the Invention

The invention relates to a device and a method for the optical selection of components of a least one fraction from a bulk material stream conveyed along a conveyance direction, having a camera unit, whose viewing direction is oriented toward the bulk material stream, a background, which is situated in the camera viewing direction behind the bulk material stream, and whose color is adaptable to the color of a selected fraction of components of the bulk material stream, an analysis and control unit, which is connected to the camera unit, and in which control commands for a separation unit, which is capable of separating the components to be selected out of the bulk material stream upon activation, may be generated according to a decision criterion.

2. Description of the Prior Art

In known facilities for the automatic optical sorting of bulk materials, the material to be sorted is applied in a single-level layer on a conveyor belt as much as possible. The conveyor belt runs at a velocity of 3 m/s, for example. At the end of the conveyor belt, the material is thrown off from the conveyor belt and flies further in a trajectory. Shortly after the ejection edge, a line-scan camera looks at the material stream. The images recorded by the camera are analyzed by a computer. The components of the bulk material stream which are to be sorted out are recognized on the basis of their color and possibly also the shape which are blown out of the free-flying material stream with the aid of short compressed air blasts. In other implementations of optical sorters, the free-flying material stream is not generated via a conveyor belt, but rather the bulk material stream slips over a chute or the bulk material stream is poured in the form of a freefalling material stream.

An important detail in the design of optical sorting devices of this type relates to the optical background, in front of which the camera records the material to be sorted. The background is typically designed in such a way that the objects to be selected and thus to be recognized stand out with sufficient contrast from the background in each case.

The first choice is a passive black background in many cases, which may easily be implemented as a light trap. If deep-black objects must also be recognized in the material stream, a homogeneous active background is selected instead, which is lite up in a color which does not occur in the bulk material—for example, a pure blue. However, this procedure is only advisable if the objects to be recognized are sufficiently large in comparison to the local resolution of the imaging optics and a camera and correspondingly sufficiently many pixels are available for recognizing color and shape of the object. In contrast, if the objects are too small, their color may no longer be reliably recognized. To solve this problem, it is fundamentally possible to increase the local resolution of the system. However, the material throughput and thus the economic utility are thus decreased at a given system performance.

In some known applications, the color of the background is selected in accordance with the color of the material to be let through, so that the material to be let through optically disappears in front of the background because of the color equalization thus provided and only the objects to be blown out stand out in front of the background with sufficient contrast. For example, if small objects of other colors are to be recognized in a material stream of small red objects, a red background would be selected, before which only the non-red objects stand out, which may then be registered by the camera unit.

The design of an adaptive background is entirely advantageous and already proven in practice. However, the difficulty results from implementing a homogeneous background in the desired color and brightness. This is true in particular if different materials are sorted on a sorting machine in relatively short chronological succession and corresponding work for changing over the background becomes necessary with each material change.

In some applications of the optical sorting of bulk materials, the objects may already be classified on the basis of their grayscale, that is, on the basis of their brightness. An analysis of the color is not necessary in these cases. In such cases, a settable background illumination is used in a known way. For the implementation, for example, a diffusely reflecting surface may be applied in the background, which is irradiated by one or more fluorescent tubes. The brightness of the background is then settable to the desired value by selection of a surface having a suitable remission factor and by regulating the lamp brightness. The local curve of the brightness over the sorting width may be adapted individually as needed, for example, by suitable screens in front of the lamps.

For the formation of a color background having a defined color, in the prior art, one or more white lamps are used and the surface applied in the background is given a suitable color. For this purpose, for example, colored adhesive films are used or the desired color tone is mixed as a colored lacquer. This method is used in sorting machines to recognize foreign bodies in tobacco, for example.

A further method according to the prior art comprises using the test subjects themselves for the production of the background color, in that a representative sample is ground and the desired color is produced from the ground material, for example.

In all of the above cases, the setting of background lighting in the color of the material flow to be let through is very complex and is only worth it if the same product is sorted on the relevant sorting machine over a longer period of time. Further disadvantages of the configurations used until now are the susceptibility of the background to contamination, fading of the color, or mismatching as a result of lamp aging. Moreover, it is only possible to produce the desired brightness curve over the entire sorting width with quite high effort.

Reference is made to the following publications in regard to the published, known prior art:

A channel sorter is described in EP 0 146 299 B1, in which a bulk material stream comprising coffee beans, for example, falls through a measuring cell. The measuring cell is composed, on the one hand, of an illuminated background and, on the other hand, a detector which has discrete photo sensors. The bulk material stream falls perpendicularly through the so-called observation zone, which is delimited by the detector having a viewing direction toward the background. If a flawed part, which stands out in color from the background, is detected in the bulk material stream, an activation of a high-pressure nozzle device, which is downstream from the measuring cell in the falling direction of the bulk material stream, is performed to select the flawed part out of the bulk material stream.

A method for the selection of flawed parts from a bulk material stream, which is based on a comparable selection principle as the previously described method, may be inferred from US 2003/0034282 A1. In this case the bulk material stream is registered by a camera unit in front of an LCD display, which represents the color background. To avoid color drifts of the color background, the color impression is registered using a spectrometer and corrected appropriately in the event of deviations.

US 2006/0016735 A1 describes a sorter for transparent granules, which fall from a belt conveyor along a trajectory through two detector units situated along the ejection path, of which one detector unit registers the front side and the other detector unit registers the back side of the granules. By comparing the registered front and back recordings, the transparency of the components may be concluded and, furthermore, flawed parts detected on the basis of a selection criterion may be sorted out of the bulk material stream using a known air pressure nozzle configuration.

SUMMARY OF THE INVENTION

The invention is a refined device and method for the optical selection of components of at least one fraction of a bulk material stream conveyed along a conveyance direction. The invention includes a camera unit, whose viewing direction is oriented on the bulk material stream, a background, situated behind the bulk material stream in the camera viewing direction, whose color is adaptable to the color of a selected fraction of components of the bulk material stream, an analysis and control unit, connected to the camera unit, in which control commands for a separation unit, which is capable of separating the components to be selected out of the bulk material stream upon activation, are generated according to a decision criterion. An increase of the performance is possible regarding sorting quality and throughput, in particular during the sorting of small objects. Furthermore, it is to be possible to adapt the color of the background, in front of which the bulk material stream is optically registered by the camera, as much as possible without great effort, preferably automatically, to the particular sorting task. The device is also usable from economic aspects in those cases in which the sorting task changes frequently and in rapid succession. Furthermore, a corresponding method allows automatic adaptation of the particle selection to different sorting tasks by the simplest possible method steps, and with the highest selection quality.

According to the invention, a device for the optical selection of components of at least one fraction from a bulk material stream, which is conveyed along a conveyance direction, is distinguished in that the camera unit is a location-resolving camera and has at least two and preferably three color channels. Each color has different spectral sensitivities. The background has a plurality of individual illuminants, of which each individual illuminant emits light having a spectral distribution which is adapted to one of the spectral sensitivity ranges of the camera in each case. Furthermore, the analysis and control unit has a unit which allows the determination of the local curve of a color value in the direction of the sorting width. The sorting width is defined as the direction transverse to the optical axis of the camera and transverse to the conveyance direction. Using this unit, the color value, which is ascertained by the camera, of the component which is not to be sorted out from the bulk material stream may be detected locally and resolved along the entire sorting width. This local curve of the color value is not necessarily constant over the entire sorting width, but rather, inter alia, subject to changes in particular at the boundary areas of the sorting width because of illumination. It is used as a basis for a regulating module, which sets the individual illuminants in regard to their brightness in such a way that the color of the background assumes the local curve of the specific color value. In this way, it may be ensured that the entire sorting width may be used in the same quality to register color differences between rejected parts and the good parts in the bulk material stream, by which the reliability in recognizing rejected parts may be improved.

Furthermore, the device according to the invention is capable of automatically setting itself to the particular sorting task, in that the color value of the fraction of the bulk material stream which is to be left uninfluenced within the bulk material stream is determined in a first step. For this purpose, a random sample of the material to be let through is put on the conveyor belt for image recording. During the image recording, the bulk material stream is vertically illuminated using lamps attached on the camera side above the bulk material stream.

To determine the color value of the fraction of the bulk material stream to be let through, the color distribution of the components of the bulk material stream is calculated, for example, in the form of color histograms. For this purpose, the color histograms are preferably ascertained as a function of the location along the entire sorting width registered by the camera unit. The sorting width is given by the camera viewing angle, the spacing between camera unit and bulk material stream, and the spatial extension of the background transversely to the conveyance direction of the bulk material stream.

During the color value determination, the background, which is also registered by the camera unit and is situated behind the bulk material stream, is either powered down, or the illuminants result in a neutral color tone on the background and cause the background to appear gray, for example, for the purpose of the most undistorted possible color value determination of the particular components to be let through in the bulk material stream. Following the image recording, a characteristic color value for the product to be let through is calculated from the measured color distribution for each location along the sorting width registered by the camera unit. For example, the maximum of the color distribution is used for the calculation.

In a next step, the background is to be adapted as identically as possible in color and brightness to the ascertained, location-related color value of the particular components contained in the bulk material stream which are to be passed. For the adaptation of color and brightness of the background, the individual illuminants assigned to the background are set in their brightness, monitored by the camera, in such a way that the best possible approximation to the local curve of the brightness and color, which were measured during the image recording, of the components of the bulk material stream to be passed results on the background. Jump in brightness or discontinuous brightness and color curves of the background are to be avoided.

To implement the smoothest possible and/or continuously appearing brightness curve of the background, a means which diffuses the light of the individual lamps is preferably provided between the bulk material stream and the plurality of the individual illuminants, preferably in the form of a diffusing panel, which prevents the camera from viewing the illuminants directly. The individual illuminants, which are preferably situated in lines or in a pattern in a plane, are activatable in regard to their brightness, either individually, that is, singly, or in small groups of particular adjacent lamps.

In a preferred embodiment, a video camera or line-scan camera is provided as the camera unit, which has individual color channels, which are each responsive separately from one another. Normal, color-capable cameras typically have three separate color channels, namely red, green, and blue having specific spectral sensitivities for the particular camera type. For example, if the color signal for "pure green" is to be generated for a given video camera, an illuminant is to be used for this purpose, whose emission spectrum is to be exclusively in the range of the spectral sensitivity of the green channel of the camera if possible. This is correspondingly true fundamentally for any arbitrary spectral sensitivity distribution of the individual color channels of cameras, which, alternatively or in a special expansion, also comprise color channels in the UV, IR, or NIR spectral ranges, for example. To meet the above requirement for the most selective possible response of the color channels of a color-capable camera, the different illuminants of the background illumination are each adapted in their spectral emission properties to one color channel of the camera unit.

In an especially preferred way, lamps in the form of LEDs, which have different colors, suggest themselves as the illuminants, the different colors each corresponding to one of the color channels of the camera. Alternatively, it is possible to implement the colors of the individual illuminants by a combination of a suitably selected light having a color filter specially adapted to the particular spectral sensitivity range of a color channel of the camera unit. Thus, color filters may also be used in combination with LEDs to minimize crosstalk if the particular emission spectrum of the LED is implemented so that the light of this LED may be detected by more than one color channel of the camera unit. Fundamentally, arbitrary illuminants which correspond to the above requirements may be used. LEDs whose emission spectra have been adapted beforehand to the spectral sensitivity range of one color channel of the camera in each case are especially advantageous.

Alternatively, for the formation of the color of the background, it is also conceivable to use a monitor unit, which has a plurality of individual, self-luminous color pixels, whose emission spectra correspond to the particular spectral sensitivity distribution of the color channels of the camera unit. Monitor units based on a cathode ray tube or monitor units based on LCD or plasma displays are suitable for this purpose.

BRIEF DESCRIPTION OF THE INVENTION

Figure 2:
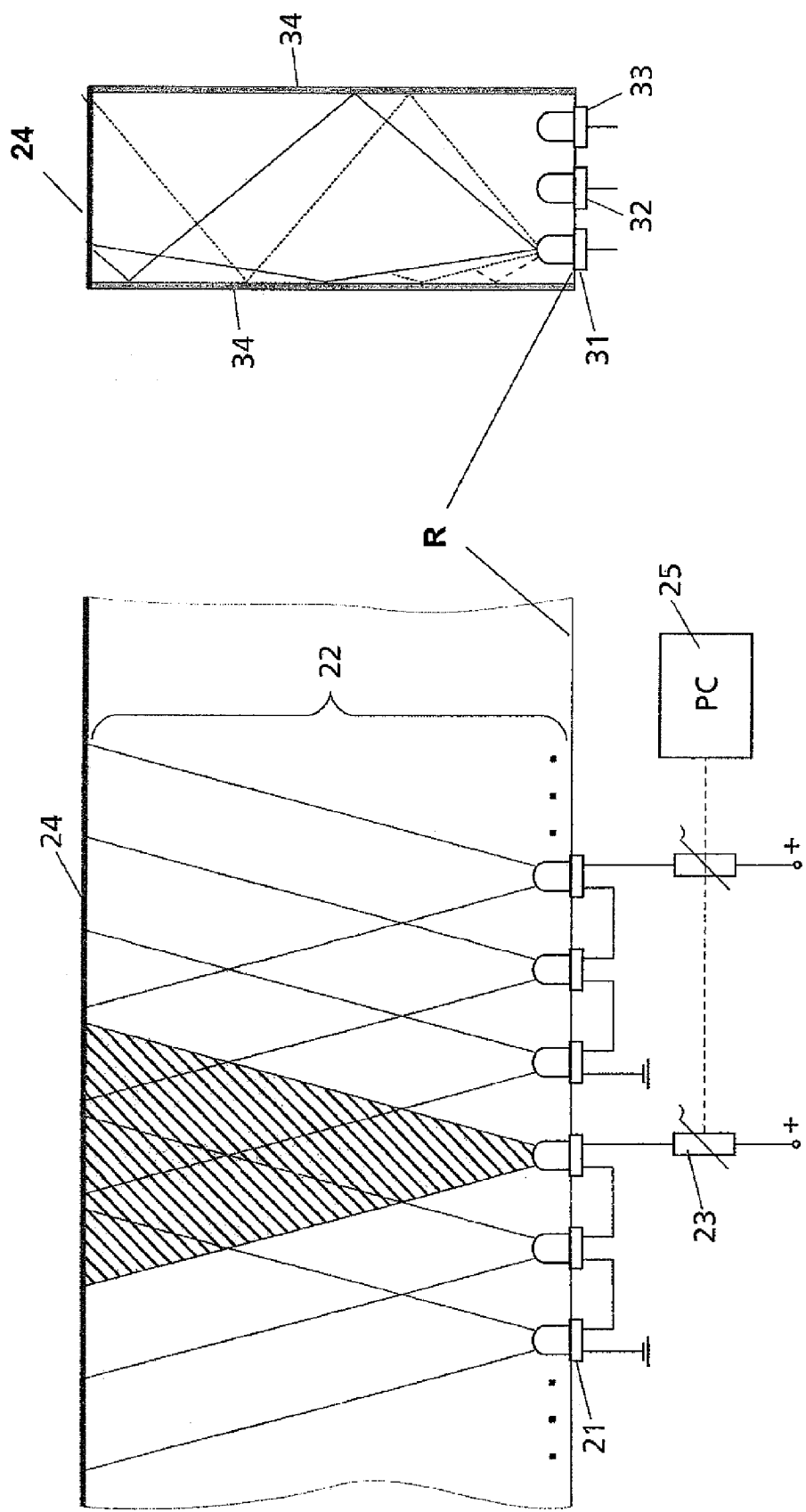
Figure 3:
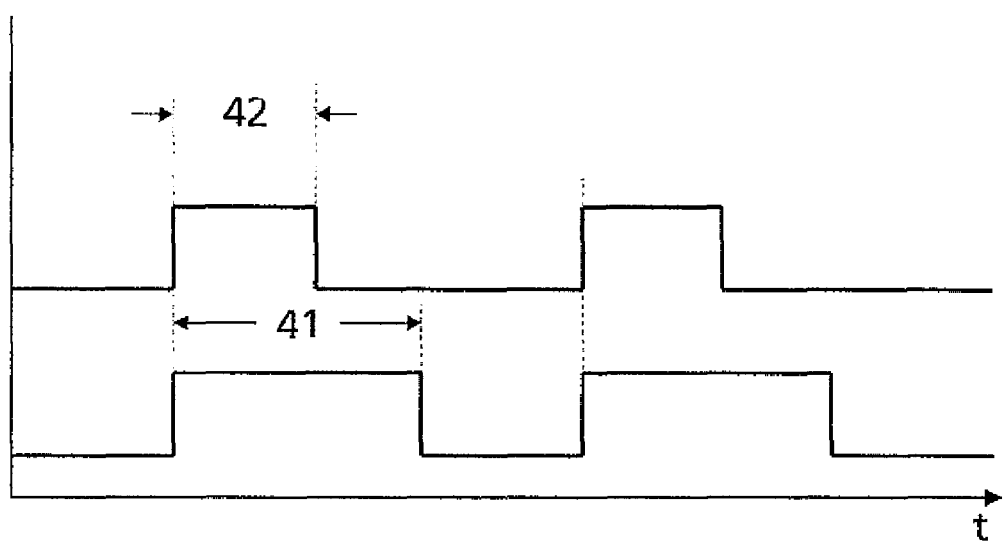
Figure 4:
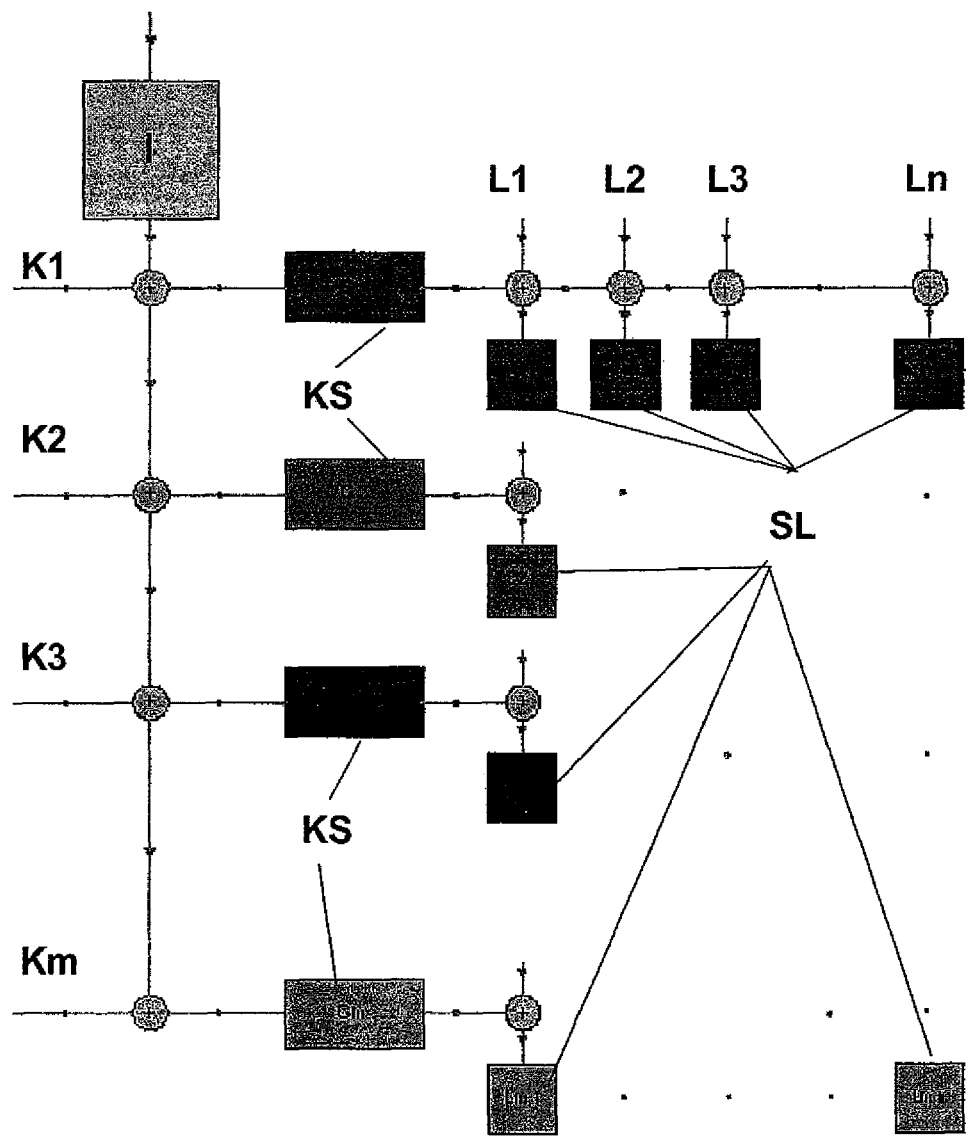

The invention is described for exemplary purposes hereafter without restriction of the general idea of the invention on the basis of exemplary embodiments with reference to the drawing. In the figures:

FIG. 1 shows a schematic illustration of a device for the optical selection of components from a bulk material stream, FIGS. 2a and b show longitudinal and cross-sectional illustrations through an adaptively adaptable background, FIG. 3 shows a time diagram to explain a pulsed-operation mode of operation of the illuminants in adaptation to the camera unit, and FIG. 4 shows a scheme to illustrate an m-channel background illumination.

DETAILED DESCRIPTION OF THE EXEMPLARY EMBODIMENTS

FIG. 1 shows the schematic construction of a device for the optical selection of components of at least one fraction, which is preferably distinguished by the color, from a bulk material stream 1 conveyed along a conveyance direction 11, which, after leaving the conveyance direction 11 along a free trajectory, is captured in a collection container (not shown in greater detail). A color-capable camera unit 12, whose viewing direction 12' registers the bulk material stream 1 in front of a background 13, whose color is adaptively adaptable, is located largely perpendicular to the free flight direction of the bulk material stream 1. Lamps 14, which illuminate the bulk material stream 1 using white light, are provided symmetrically to the viewing direction 12' of the camera unit 12 to illuminate the bulk material stream 1. The special feature of the device is that the background 13 is adapted in regard to color and brightness to those components within the bulk material stream 1 which do not have to be sorted out and therefore also do not have to be registered. Upon successful adaptation, the camera unit 12 is not capable of recognizing the components of the bulk material stream 1 to be let through in relation to the background, which is identical in color and brightness. However, if different colored components are present within the bulk material stream 1, they are recognized by an analysis and control unit 18. A compressed air nozzle unit 15, which is capable of separating the different-colored components 17 by compressed air blast out of the bulk material stream 1, is activated for the selection of different components of this type within the bulk material stream 16.

FIG. 2a shows a longitudinal sectional illustration through the background provided with the reference numeral 13 in FIG. 1. The illustration in FIG. 2b corresponds to a cross-sectional illustration through the background 13. The background 13 encloses a cuboid volume in the illustrated exemplary embodiment, on whose rear wall R illuminants 21 implemented as LEDs are situated adjacent to one another in rows and columns. A diffusing panel 24, which the viewing direction of the camera unit 12 is oriented toward, is provided opposite to the rear wall R. The diffusing panel 24 is a surface which diffuses in transmission. The lamps 21, implemented in FIG. 2a as a small group of adjacent LEDs, have a uniform emission spectrum and may be regulated in their brightness via a shared actuator 23 by an analysis and control unit 25 in the form of a PC computer. The illuminants 21 situated on the rear wall R are spaced apart from the diffusing panel 24 by the superposition distance 22, so that the brightness existing at the location of the diffusing panel results by superposition of the light beams of all illuminants attached to the rear wall. In this way, it is ensured that a smooth brightness curve results from the viewing angle of the camera along the observation width, or along the sorting width, on the background in spite of the use of a plurality of discrete individual lamps.

To make the background appear in a specific color tone at the location of the diffusing panel 24, the individual lamps 21 are divided into classes in accordance with the color channels of the camera 12 and it is concurrently ensured that the emission spectra of the individual color classes are adapted to the spectral sensitivity of one of the color channels of the camera 12 in each case. This may either be implemented in that the individual illuminants are implemented as white light lamps in combination with corresponding color filters, or the individual illuminants are implemented as LEDs having correspondingly selected emission spectra, for example.

To illustrate a configuration having illuminants divided into three color classes, reference is made to the cross-sectional illustration in FIG. 2b, which shows three rows of lamps having different colors. Thus, the lamps 31 shown in the first row have the emission spectrum E1, the lamps 32 have the emission spectrum E2, and the lamps 33 have the emission spectrum E3. If a typical color camera is used as the camera unit 12, the individual emission spectra E1, E2, and E3 correspond to the colors red, green, and blue.

Because of the superposition distance 22 existing between the rear wall R and the front diffusing panel 24, the light components of all illuminants E1, E2, and E3 are superimposed at the location of the diffusing panel 24 to implement a homogeneous color mixed tone. The mirrored side walls 34, which connect the rear wall R to the diffusing panel 24, ensure, on the one hand, that all of the light originating from the illuminants is incident on the diffusing panel 24 and, on the other hand, that the brightness distribution on the diffusing panel 24 is constant.

The configuration of the illuminants sketched in FIGS. 2a and b comprises three lines of lamps, the lamps of each line being assignable to one color class. Notwithstanding this configuration, however, other geometric configurations of the illuminants along the rear wall R of the background shown in FIGS. 2a and b are also conceivable.

For the automatic adaptation of the background illumination, it is necessary for all individual illuminants or the illuminants combined into groups in each case to be settable in regard to their brightness by an analysis and control unit. Computer-controlled actuators 23 are used for this purpose, as may be inferred from the exemplary embodiment according to FIG. 2a. Actuators for variation of the current or the operating voltage for the individual lamps are particularly suitable for setting the brightness. A further possibility for brightness setting is provided by a pulsed voltage or power supply, the brightness of the lamps being able to be varied by suitable selection of the pulse widths.

If LEDs are used, they are each capable of each generating light flashes upon pulsed activation. In connection with commercially available line-scan cameras, this type of brightness control is only advisable if the control pulses for the light diodes are synchronized with the integration time of the camera. A time diagram is shown for this purpose in FIG. 3, in which, on the one hand, the intervals 41 for the integration time of the camera and, on the other hand, the control pulses 42, which are synchronized with these intervals 41, for activating the LEDs or groups of LEDs are shown. In this implementation, every moment for turning on all LEDs is identical, but the pulse duration is individually selectable for every group of LEDs.

With the aid of the device according to the invention, it is possible to perform an adaptation of the background to the color of the components of a bulk material stream to be passed completely automatically after appropriate color determination of the components to be passed in each case. The color adaptation of the background is performed in a first step by measuring the color distribution for the components of the bulk material to be passed. This measurement is performed for every location which may be registered by the camera along the color adaptable background. For this purpose, the adaptive background illumination is set to a neutral color, for example, such as gray, while the bulk material runs through the sorting device. In a second step, the ascertainment of the characteristic local curve of the color for the components of the bulk material stream to be passed is performed, for example, by calculating the focal point or the maximum values from the color distributions measured for each location. Furthermore, the brightness is set for the individual LEDs or groups of LEDs provided in the background in such a way that the color curve of the background corresponds to the ascertained characteristic local curve of the color of the components of the bulk material stream to be let through. The brightness setting and, connected thereto, the color adaptation of the background are preferably performed in the context of an iterative equalization method.

A further configuration for activating the illuminants assignable to the background is shown in FIG. 4, which, in contrast to the exemplary embodiment explained above, has illuminants which may be divided into m spectral channels $K_1, \ldots, K_m$. It is thus assumed that n individual illuminants $L_1, \ldots, L_n$ are provided for each of the m spectral channels $K_1, \ldots, K_m$, whose brightnesses are to be set individually for an adaptive adaptation of the overall color curve, which is to be generated using the background, to the local curve of the color value obtained in the preceding way for the components to be accepted in the bulk material stream. Furthermore, it is assumed that the m spectral channels subdivide a spectral range extending from UV-C to MID-IR. Each individual illuminant $L_i$ within the particular m spectral channels, or each group of illuminants, is activated individually by an actuator SL for the brightness adaptation. To set the overall brightness of all illuminants $L_{j1}, \ldots, L_{jn}$ associated with a spectral channel $K_j$, it is advisable to previously link the activation channels for the individual actuators SL to an overall brightness signal for the particular channel. This is performed in each case via a channel actuator KS. If the actuators are linked as shown in FIG. 4, the overall brightness of the illumination may additionally be regulated using a single main actuator I.

The sorting method according to the invention may thus be applied for components in bulk material streams which have a largely arbitrary coloration. Requirements for a successful application of the method in this regard are imaging sensors and light sources which may be spatially modulated for the particular observed spectra range. For example, the spectral ranges from UV-C to MID-IR may be completely covered using LEDs.

If the individual m spectral channels are sufficiently separated from one another both on the side of the illumination and also on the side of the light detection, each channel may be handled alone. The principle may therefore be implemented in m channels (with m being theoretically infinite) and offers the following advantage for each spectral channel:

Common camera systems typically have a characteristic sensitivity curve over the sorting width to be observed for image recordings having vertical illumination. This curve may be equalized by the adaptation of the brightness curve of the background to the brightness curve for the main component of the bulk material stream. The brightness of the imaged main component of the bulk material stream may thus correspond to the brightness of the background at every point of the inspection line. The main component of the material stream thus becomes "invisible" for the image processing. In the ideal case, only deviations therefrom are visible. The image processing is accordingly relieved and/or simplified.

In multichannel configurations, a deviating color and/or brightness curve is typically provided for each channel. However, by using components of extreme quality, for example, apochromatic objectives, etc., an identical sensitivity curve may be achieved for all inspected spectral ranges. Therefore, each spectral channel may be set per se using configurations according to the exemplary embodiment shown in FIG. 4. The above-mentioned advantage is thus obtained for each individual channel. The requirement for an identical curve of the sensitivity may thus be dispensed with and equally good sorting may be achieved using correspondingly simpler components.

The setting of the background color in m spectral channels is preferably performed in each channel in a three-step process. In the first step, the background is set to a contrast value for the product brightness, that is, the brightness which the components, which are not to be sorted out in the bulk material stream, have. The second step is used for learning the product brightness in front of precisely this background, and in the third step the background illumination assumes the product brightness ascertained in step two.

The first and third process steps each represent iterative processes, which may themselves be divided in turn into five partial steps. In partial step one, the assignment of the individual illuminants to the pixels of the camera is produced firstly for each channel of the camera. In an iteration method, the control value of the actuator KS (see FIG. 4) is varied until the maximum of the brightness curve of the current channel is approximately half of the target brightness (partial step two). To arrive at the desired overall brightness, in partial step three, each individual illuminant is switched on in sequence, for example, from left to right, each controlled via the actuators SL, also in iterative steps. The iteration for an illuminant is ended as soon as the target brightness is reached in the area of the previously established pixel assignment. Partial step four represents a repetition of partial step three in the reverse direction (for example, from right to left). In partial step five, the results of the two measurement sequences, that is, partial steps three and four, are averaged and thus represent the final values for the actuators SL.

If the background illumination is designed in such a way that no crosstalk occurs between the individual m channels, the setting of the m channels may be performed individually in the way described for one channel. The brightness of all m*n illuminants may be set while maintaining the ratios of the brightnesses of the m*n illuminants to one another by the actuator I according to FIG. 4.

If crosstalk occurs between the m channels, it is advantageous to take this crosstalk into consideration during the setting. In the case of an iterative setting, the channels are set in the sequence of their crosstalk. In certain circumstances, it may be advantageous to optimize the overall result over the channels in a further iteration.

During a setting based on the characteristic curve of the background illumination, the pixel brightness may be ascertained as a function of all m*n illuminants for each of the m channels. The calculation of the control variables for each of the illuminants is then performed similarly to the calculation described above, but m*n dimensionally.

List Of Reference Numerals
1 bulk material stream
11 conveyance direction
12 camera unit
12' viewing direction of the camera unit
13 background
14 illumination lamps
15 separation unit
16 bulk material stream which is let through
17 components to be separated
21 illuminant, LED
22 superposition distance
23 control element
24 scattering disk
25 analysis unit, PC computer
31, 32 and 33 red/green/blue LED
34 mirrored walls
41 integration time of the camera unit
42 pulse width of an LED flash
L1-Ln illuminant
SL actuator illuminant
KS actuator spectral channel
K1-Km spectral channels
I actuator overall configuration

The invention claimed is:

1. A device for the optical selection of at least a fraction of components from a bulk material stream conveyed along a conveyance direction, including a camera, with a camera viewing direction oriented on the bulk material stream, a background, situated behind the bulk material stream in the camera viewing direction, having a color adaptable to a color of a selected fraction of the components of the bulk material stream, an analysis and control unit, coupled to the camera, for providing control of a separation unit, the separation unit controlling selection of components from the bulk material stream according to a decision criterion, wherein:
the camera unit provides local resolution and has at least two color channels each having different spectral sensitivity;
the background is illuminated by a plurality of illuminants, each illuminant emitting light with a spectral distribution adapted to a spectral sensitivity of the camera; and
the analysis and control unit determines at least one local color value of a component of the bulk material stream transverse to the conveyance direction and regulates setting brightness of the illuminants so that the color of the background assumes the at least one local color value.

2. The device according to claim 1, wherein:
the camera comprises a video camera or line-scan camera, with at least three color channels including a red color channel, a green color channel, and a blue color channel.

3. The device according to claim 1, wherein:
the spectral distribution of light provided by each illuminant is exclusively detectable by a single color channel of the camera.

4. The device according to claim 1, wherein:
the illuminants are adjacent to each other and are located either in a line or in a pattern within a plane.

5. The device according to claim 1, wherein:
the illuminants comprise LEDs which are in groups which provide a spectral emission corresponding to the color channels of the camera.

6. The device according to one of claim 1, wherein:
the illuminants which are provided in at least one color channel each include at least one light source and one color filter.

7. The device according to claim 1, wherein:
the background includes a means for diffusing light emitted by the illuminants.

8. The device according to claim 7, wherein:
the light emitted by the illuminants is superimposed.

9. The device according to claim 8, wherein:
at least one means for superimposing the light and/or a distance between the illuminants and the background is provided for superimposing the light and further comprising mirrored surfaces forming a mirrored channel between the illuminants and the means for diffusing light emitted by the illuminants.

10. The device according to claim 1, wherein:
at least one optical imaging element is provided between the illuminants and the camera which images or focuses a point of light emitted by each illuminant in the direction of the camera unit.

11. The device according to claim 10, wherein:
the at least one optical imaging element is a cylindrical lens.

12. The device according to claim 10, wherein:
each illuminant includes an optical imaging element.

13. The device according to claim 1, wherein:
the background comprises a monitor comprising one of an x-ray device, an LCD display screen, or a plasma display screen, and the illuminants are luminous color pixels of the monitor.

14. The device according to claim 1, wherein:
the analysis and control unit for providing a brightness setting of the illuminants and includes at least one actuator for setting a supply current and/or a supply voltage of each illuminant and/or a pulse unit for generating control pulses for application to the illuminants so that brightness of the illuminants is settable via a selection of the voltage, the current and/or a pulse sequence of the control unit.

15. The device according to claim 1, wherein:
the separation unit comprises a nozzle to which compressed air may be applied to provide targeted compressed air pulses for removing components from the bulk material stream.

16. The device according to claim 1, wherein:
the analysis and control unit obtains local information regarding brightness and color of the components and information regarding sorting width, defined in a direction transverse to the conveyance direction of the bulk material stream and to an optical axis of the camera.

17. The device according to claim 16, wherein:
a regulating module locally adapts the background regarding brightness and color based upon the local information regarding color along the sorting width viewed by the camera.

18. A method for optical selection of at least a fraction of components from a bulk material stream conveyed along a conveyance direction, in which the bulk material stream is positioned along a sorting width using a camera in front of a colored background, which is changeable in color, and the color thereof is changed to the color of a selected fraction of components of the bulk material stream, and components of the bulk material stream which are not included in the selected fraction are separated out of the bulk material stream by a separation unit, comprising:

setting, at least once, local colored background based control variables which are repeatedly ascertained over time or in a learning procedure;

continuously locally detecting components in the bulk material stream, which differ in color from the colored background, along the sorting width by using the camera; and separating the locally detected components from the bulk material stream which differ from the colored background.

19. The method according to claim 18, wherein:
values of the control variables for changing the colored background are calculated from the color of a fraction of the bulk material stream, at least one characteristic of the camera, at least one illuminator or the colored background.

20. The method according to claim 18, wherein:
the learning procedure selects a color value of the selected fraction of the bulk material stream in front of the color background which is locally detected and the background is color neutral or is a gray color tone.

21. The method according to claim 18, wherein:
ascertaining local color of the components is performed as part of a focal point calculation or a maximum calculation from a local color distribution, in which the focal point or the maximum calculation is for each location along the sorting width.

22. The method according to claim 18, wherein:
changing of brightness and color of the color background within the learning or setting is performed by iterative regulation of brightness of illuminants or groups of illuminants which determine a color of the color background.

23. The method according to claim 22, wherein:
the setting or learning procedure comprises:
a) setting, the background to a contrast value for the brightness of the selected fraction;
b) learning the brightness of the selected fraction in front of the background; and
c) using the learned brightness of the selected fraction to illuminate the background.

24. The method according to claim 23, wherein:
steps a) and c) comprises:
T1) assigning individual illuminants to individual color channels of the camera;
T2) setting all illuminants brightnesses of each spectral channel using an actuator until a maximum of a brightness of the each spectral channel is approximately half of a target brightness;
T3) iteratively adjusting each individual illuminant by control of actuators until a target brightness is reached;
T4) repeating step T3) with an altered sequence during the setting of brightness of the illuminants; and
T5) averaging brightness values obtained in steps T3) and T4) and setting the actuators based on averaged brightness values.

* * * * *